(12) United States Patent
Hill et al.

(10) Patent No.: US 6,641,561 B1
(45) Date of Patent: Nov. 4, 2003

(54) DRUG DELIVERY DEVICE

(75) Inventors: Robert L. Hill, Abingdon, MD (US); John G. Wilmot, Mt. Airy, MD (US); Steven Griffiths, Ellicott City, MD (US)

(73) Assignee: Meridian Medical Technologies, Inc., Columbia, MD (US)

(*) Notice: Subject to any disclaimer, the term of this patent is extended or adjusted under 35 U.S.C. 154(b) by 0 days.

(21) Appl. No.: 09/897,422

(22) Filed: Jul. 3, 2001

Related U.S. Application Data
(60) Provisional application No. 60/238,458, filed on Oct. 10, 2000, provisional application No. 60/238,448, filed on Oct. 10, 2000, and provisional application No. 60/238,447, filed on Oct. 10, 2000.

(51) Int. Cl.[7] .......................... A61M 5/20; A61M 37/00
(52) U.S. Cl. ........................................ 604/136; 604/89
(58) Field of Search .................................. 604/131, 134, 604/135, 136, 139, 190, 191, 192, 82, 89, 90, 91

(56) References Cited

U.S. PATENT DOCUMENTS 3,757,779 A * 9/1973 Rovinski ..................... 604/190
3,863,624 A    2/1975 Gram (List continued on next page.)

FOREIGN PATENT DOCUMENTS

| DE | 1 961 166 | 7/1970 |
|---|---|---|
| EP | 0 112 574 | 7/1984 |
| EP | 0 511 183 A1 | 10/1992 |
| WO | WO 94/09839 | 5/1994 |

*Primary Examiner*—Sharon Kennedy
*Assistant Examiner*—Mark K. Han
(74) *Attorney, Agent, or Firm*—Pillsbury Winthrop LLP (57) ABSTRACT

The present invention is directed to a drug delivery device. The device includes an interior chamber and a seal structure. In accordance with the present invention, the interior chamber may include a first, liquid medicament compartment and a second medicament compartment. The seal structure is conditionable to permit fluid to pass therethrough upon pressurization of the fluid. The seal structure preferably includes a sealing member which moves from a first sealed position into a second by-pass position upon pressurization of the liquid injection solution in the wet compartment of the housing assembly. Such by-pass movement of the sealing member enables the liquid injection solution to flow through the seal structure into the second ingredient compartment and mix for injection.

33 Claims, 8 Drawing Sheets

U.S. PATENT DOCUMENTS

| | | |
|---|---|---|
| 4,060,082 A | 11/1977 | Lindberg et al. |
| 4,413,991 A | 11/1983 | Schmitz et al. |
| 4,529,403 A | 7/1985 | Kamstra |
| 4,613,326 A | 9/1986 | Szwarc |
| 4,755,169 A * | 7/1988 | Sarnoff et al. ............... 604/136 |
| 4,792,329 A | 12/1988 | Schreuder |
| 4,822,340 A | 4/1989 | Kamstra |
| 4,861,335 A | 8/1989 | Reynolds |
| 4,874,381 A | 10/1989 | Vetter |
| 4,898,580 A | 2/1990 | Crowley |
| 4,983,164 A | 1/1991 | Hook et al. |
| 4,994,043 A | 2/1991 | Ysebaert |
| 5,015,229 A | 5/1991 | Meyer et al. |
| 5,041,088 A | 8/1991 | Ritson et al. |
| 5,080,649 A | 1/1992 | Vetter |
| 5,281,198 A | 1/1994 | Haber et al. |
| 5,295,965 A | 3/1994 | Wilmot |
| 5,298,024 A | 3/1994 | Richmond |
| 5,354,286 A | 10/1994 | Mesa et al. |
| 5,391,151 A | 2/1995 | Wilmot |
| 5,429,603 A | 7/1995 | Morris |
| 5,465,727 A | 11/1995 | Reinhold, Jr. |
| 5,472,422 A * | 12/1995 | Ljungquist ................... 604/518 |
| 5,569,192 A | 10/1996 | Van der Wal |
| 5,620,421 A | 4/1997 | Schmitz |
| 5,637,087 A | 6/1997 | O'Neil et al. |
| 5,725,777 A | 3/1998 | Taylor |
| 5,785,683 A | 7/1998 | Szapiro et al. |
| 5,807,344 A | 9/1998 | Iwasaki |
| RE35,986 E | 12/1998 | Ritson et al. |
| 5,971,953 A | 10/1999 | Bachynsky |
| 6,093,172 A * | 7/2000 | Funderburk et al. ......... 604/131 |
| 6,149,628 A * | 11/2000 | Szapiro et al. .............. 604/191 |
| 6,379,328 B1 * | 4/2002 | Mac Clay ................... 604/191 |
| 2002/0049407 A1 | 4/2002 | Hill et al. |

* cited by examiner

DRUG DELIVERY DEVICE

RELATED APPLICATIONS

This application is related to and claims priority to provisional U.S. Patent Application Nos. 60/238,458, 60/238,448 and 60/238,447, all filed on Oct. 10, 2000, all under the title of "Wet/Dry Automatic Injector Assembly," and all of which are incorporated herein by reference.

FIELD OF THE INVENTION

The present invention relates to drug delivery devices for delivering a medicament. In particular, the present invention is directed to an automatic injector assembly for quickly combining two components to form a liquid medicament, and delivering the liquid medicament to an injection site.

BACKGROUND OF THE INVENTION

An automatic injector is a device that enables intramuscular (IM) or subcutaneous administration of a dosage of medicament. Generally, the medicament is stored as a liquid formulation which is then injected intramuscularly. An advantage of automatic injectors is that they contain a measured dosage of a liquid medicament in a sealed sterile cartridge. As such, automatic injectors allow for quick and simple IM injection of a liquid medicament in emergency situations without the need for measuring dosages. Another advantage of automatic injectors is that the administration of the medicament is accomplished without the user initially seeing the hypodermic needle through which the medicament is delivered, and without requiring the user to manually force the needle into the patient. This is particularly advantageous when the medicament is being self-administered.

There are drawbacks associated with the long-term storage of medicament in a liquid formulation. For instance, some medicaments are not stable in solution and thus have a shorter shelf life than their solid counterparts. To address this concern, automatic injectors have been developed which store the medicament in solid form and mix the solid medicament with a liquid solution immediately prior to injection. These injectors, disclosed for example in U.S Re. issue Pat. No. 35,986, entitled "Multiple Chamber Automatic Injector," (the disclosure of which is incorporated herein specifically by reference), however, require the user of the injector to manually rupture a sealing member between the solid and liquid components and then manually shake the injector body to expedite dissolution of the solid component prior to injection. This increases the time needed to administer a dose of the medicament. However, rapid delivery of the medicament is needed in many emergency medical situations (e.g., nerve gas and chemical agent poisoning). Other wet/dry injection devices have been expensive to manufacture or provided unsatisfactory mixing of components prior to injection. Therefore, there is a need for a cost-effective automatic injector that stores medicament in solid form that does not require manual premixing by the user.

SUMMARY OF THE INVENTION

In response to the foregoing challenges, applicants have developed an innovative automatic injection device containing a pre-loaded charge of medicament for automatically administering the medicament upon actuation thereof. The automatic injection device comprises a housing assembly and a chamber disposed within the housing assembly. The interior chamber includes a dry compartment for storing a predetermined charge of dry medicament therein, and a wet compartment for storing a predetermined amount of liquid injection solution therein. A seal structure is disposed to seal the dry compartment from the wet compartment while the injection device is in storage. The seal structure permits the liquid injection solution to pass therethrough and mix with the dry medicament to form a medicament mixture within the chamber during an injection operation. A needle assembly is in communication with the medicament mixture during the injection operation to enable administration of the medicament mixture. A plunger is disposed within the chamber and is movable through the chamber during the injection operation to force the medicament mixture through the needle for administration of the medicament mixture. A stored energy activation assembly is operable to release stored energy that forces the plunger through the chamber during the injection operation. The seal structure is conditionalable in response to operation of the activation assembly to permit the liquid solution to pass therethrough and mix with the dry medicament as aforesaid.

Other aspects and advantages of the present invention will become apparent from the following detailed description, drawings and claims.

BRIEF DESCRIPTION OF THE DRAWINGS

The invention will be described in conjunction with the following drawing in which like reference numerals designate like elements and wherein.

DETAILED DESCRIPTION OF THE PREFERRED EMBODIMENT

Figure 1:
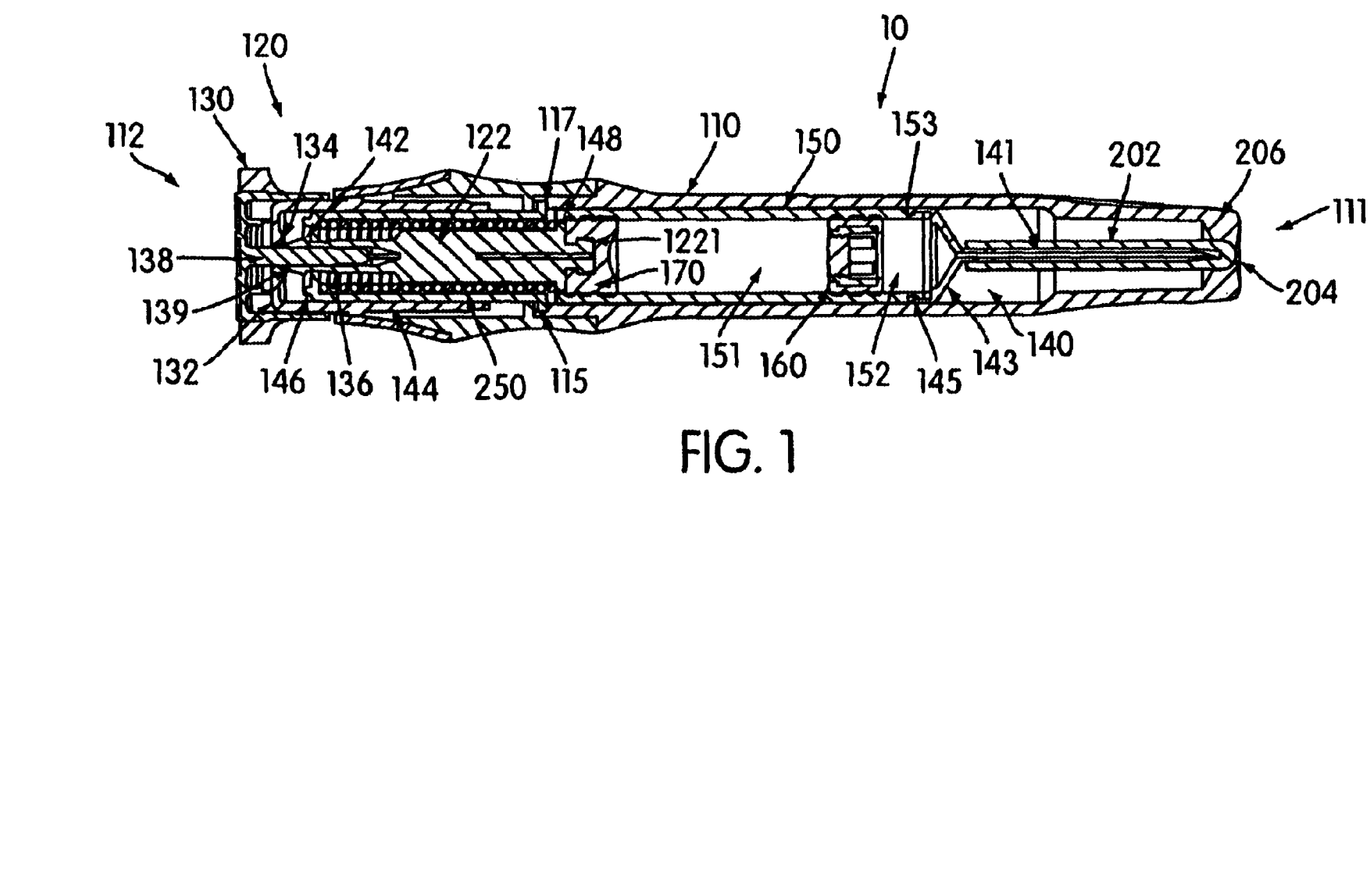
FIG. 1 is a longitudinal cross-sectional view of a wet/dry automatic injector assembly in accordance with an embodiment of the present invention.

Referring now, more particularly to the figures, there is shown in FIG. 1 an automatic injector assembly 10 in accordance with an embodiment of the present invention. The present invention is described in connection with a push button type auto injector, whereby the user removes an end cap assembly and presses a button to trigger the injection process. The present invention, however, is not limited to push button type automatic injectors; rather, it is contemplated that the present invention may be incorporated into a nose activated auto injector, as described for example in U.S. Pat. No. 5,354,286, the disclosure of which is hereby incorporated herein by reference for such teaching.

The automatic injector assembly 10 includes a generally hollow tubular plastic housing 110. Generally, the housing 110 includes an injection end 111 and an activation end 112, as shown in FIG. 1. In the embodiment shown, an actuator assembly 120 is inserted into the rearward end of the housing 110. The actuator assembly 120 is received within the housing 110 until flange 115 of a sleeve member 144 snaps into annular groove 117 on the interior surface of housing 110. A removable safety cap 130 is releasably secured to the actuator assembly 120.

The actuator assembly 120 is of any conventional type as known in the art, such as that disclosed in commonly assigned U.S. Pat. No. 5,391,151 hereby incorporated by reference. The present invention employs a rear-end activating device, similar to that in the aforementioned U.S. Pat. No. 5,391,151, and is therefore only briefly discussed herein. The actuator assembly 120 includes an activation button sleeve 132 having internal activation surfaces 134. The activation assembly further includes a plastic collet 122 with a split rearward portion forming spring fingers 136 as known in the art. The safety cap 130 has a pin portion 138 that extends between the spring fingers 136 so as to keep them spread apart when the injector is in a storage condition. The spring fingers 136 terminate in semi-conical configurations including rearwardly facing sloping surfaces 139 and forwardly facing flat surfaces 142. The collet 122 is surrounded by a cylindrical sleeve 144 having inwardly extending flange 146 at the rearward end thereof. The collet 122 has a forward annular flange 148. A coil spring 250 surrounds the collet 122 and is compressed between the flange 148 and flange 146. The collet flat surfaces 142 are retained in engagement with the rearwardly facing surfaces of the flange 146, and thus prevented from moving off of the flange surfaces by the pin 138 when the injector is stored.

To activate the injector, the safety pin 130 is manually pulled off of the rear end of the injector, thus removing pin 138 from between the fingers 136. The activation button 132 can then be pushed inwardly, and as a result of the activation surfaces thereof, 134 engages the sloping surfaces 139 of the spring fingers 136. This forces the spring fingers 136 inwards toward one another and off of the retaining surfaces of the flange 146. The compressed spring 250 is then free to release the stored energy therein to move the collet 122 forwardly under the force of the spring to affect an injection operation as will be described later in more detail.

It is contemplated that the actuator assembly 120 can be of any type known in the automatic injector art that employs releasable stored energy. For example, rather than emptying a spring, it may employ a charge of compressed gas.

Located within the interior of the housing 110 is a vial or chamber 150, preferably made of glass, for containing both the liquid injection solution and the dry medicament. The chamber 150 is preferably a hollow cylinder, with a smooth cylindrical inner surface. The liquid injection solution is located within a wet portion 151 of the chamber 150. The dry medicament is located within a dry portion 152 of the chamber 150. It is contemplated that the dry medicament may be in powder, lyophilized, freeze-dried, or any other solid formulation known in the art. A seal structure 160 engages the interior side walls of the chamber 150 to seal the dry portion 152 from the wet portion 151 and to prevent seepage of the liquid injection solution into the dry portion 152 prior to activation of the injector assembly. Further, a needle assembly 140 mounts to the forward end of vial or chamber 150 to inject the medicament upon activation of the injector assembly. In this embodiment, the forward end portion of the chamber 150 has an annular groove 153 formed therein for attachment of the needle assembly 140. The needle assembly 140 includes a funnel-shaped needle support 143. The wide end of the needle support 143 has an annular rib 145 that is snap-fit into groove 153 to form a seal with the chamber 150. The needle support 143 can be made of a resilient plastic material, or metal with a rubber seal that seats into groove 153. The forward narrow end 147 (see FIG. 2A) of the needle support 143 sealingly receives the rearward end of hollow needle 141. The needle support 143 forms a sealed fluid channel from the chamber 150 to the needle 141. A rubber needle sheath 202 surrounds the needle 141 and receives the narrow end 147 of the needle support 143. A filter 190 is sealingly retained across the entire wide-end mouth of the needle support 143 by an annular sealing washer 156.

Figure 2A:
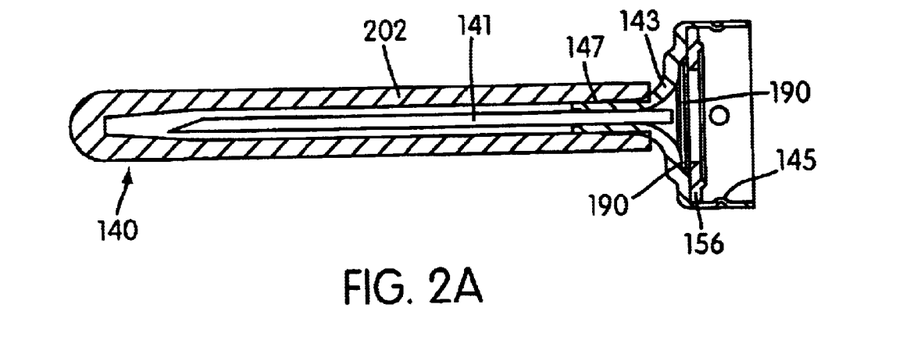
FIGS. 2A–2B illustrate longitudinal cross-sectional views of needle support assemblies in accordance with certain embodiments of the present invention.
Figure 2B:
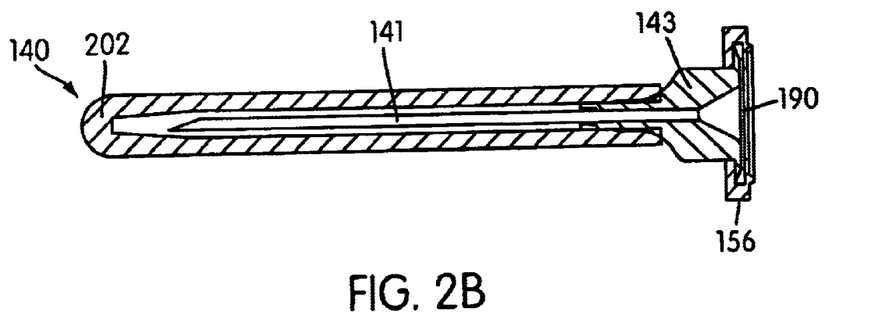
Figure 3A:
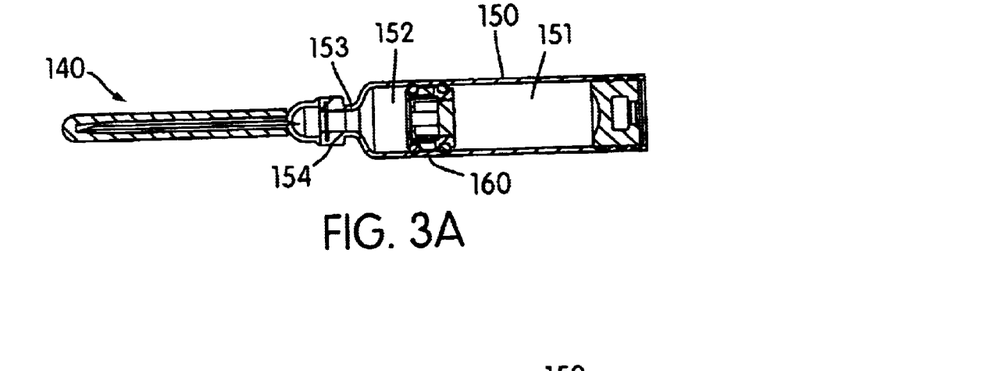
FIGS. 3A–3D illustrate cross-sectional side views of various cartridge or chamber configurations and corresponding needle assembly options according to certain embodiments of the present invention.
Figure 4:
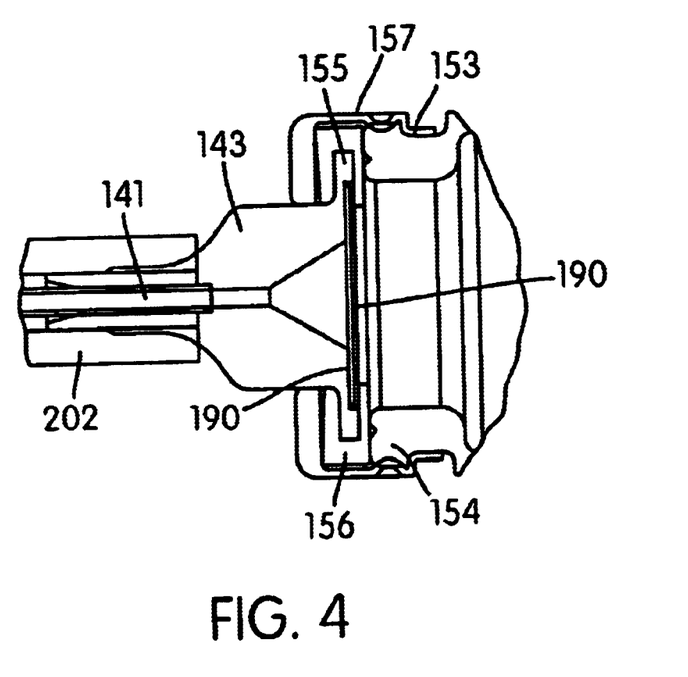
FIG. 4 is an enlarged partial cross-sectional side view of a needle assembly/cartridge engagement according to the embodiment illustrated in FIG. 3A.

FIGS. 2B, 3A, and 4 illustrate another embodiment of a needle assembly 140 and chamber 150. The chamber 150 in this embodiment is known in the art as a dental cartridge. The dental cartridge has a cylindrical rear portion and a narrowed forward neck portion defining an outer annular groove 153. The forward end of the dental cartridge defines an annular flange portion 154. In this embodiment, the needle support 143 has a rearward annular flange 155 that receives an annular sealing member 156 that surrounds both sides of flange 155. The sealing member 156 serves to seal a filter 190 over the wide end of the funnel shaped needle support 143. The rearward surface of the sealing member 156 is sealingly clamped against the forward surface of chamber flange 154 by a metal retaining clamp 157 as best seen in FIG. 4.

Returning to FIG. 1, forward end 1221 of the collet 122 extends into the rearward end of chamber 150 and is adapted to connect with a plunger 170 rearwardly sealing the wet container 151. The plunger 170 is adapted to sealingly engage the side wall of the wet container 150 to prevent leakage of the contents (e.g., liquid injection solution) of the wet container 151. The plunger 170 is preferably formed from a material having low frictional properties such that the collet 122 and plunger 170 may easily slide within the wet container 150 when operated. Alternatively, the plunger 170 may be lubricated with silicon or other suitable non-reactive lubricant. The movement of the collet 122 and the plunger 170 pressurizes the liquid located within the wet container 151. A suitable medicament is located within a dry container 152.

Figure 3B:
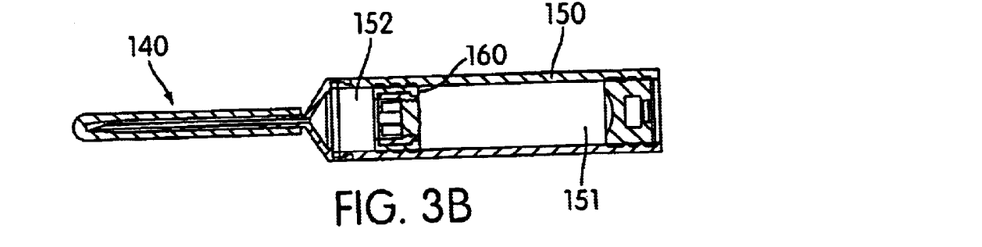
Figure 3C:
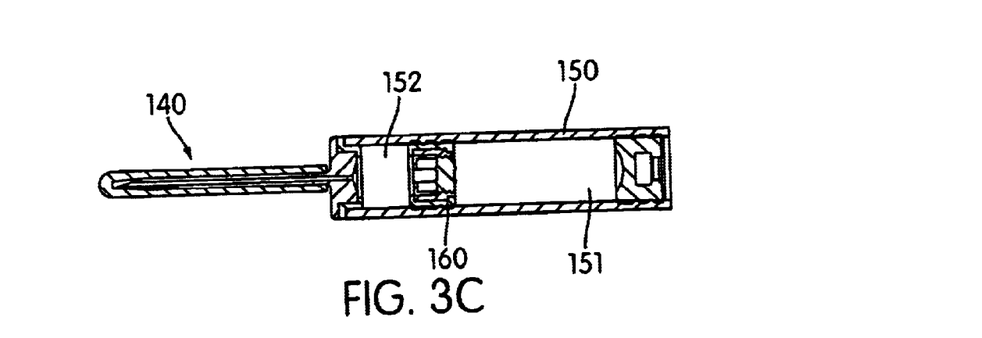
Figure 3D:
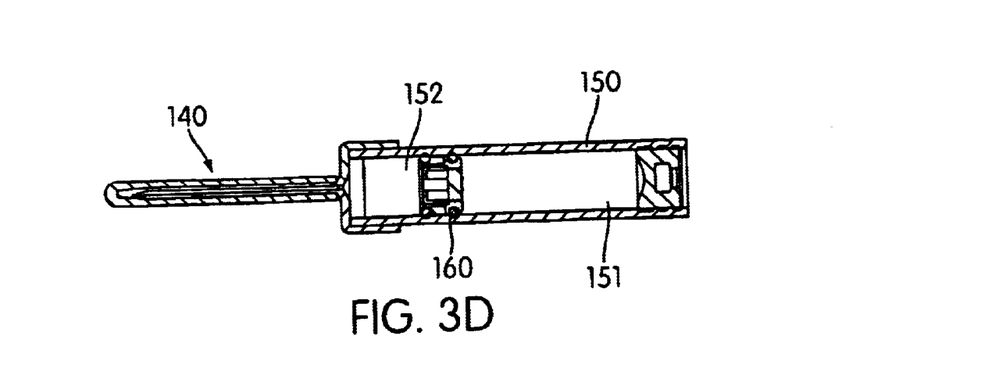

The embodiment of FIGS. 1 and 2A is advantageous in that it has an open mouth configuration wherein the needle-end of the vial or chamber is not significantly narrowed or tapered. Such an open mouth configuration permits direct access to the dry portion 152 of chamber 150 for easy loading. Further, the open mouth configuration aids in preventing cross contamination between wet portion 151 and dry portion 152 in that the dry portion 152 does not have to be filled through liquid portion 151 of chamber 150. Needle assembly 140 can be mounted to vial or chamber 150 in a snap-on configuration (FIG. 3B), an internal mount configuration (FIG. 3C), or an external needle assembly configuration (FIG. 3D).

As mentioned above, the seal structure 160 is adapted to engage the interior side walls of chamber 150 to prevent passage of the contents (e.g., liquid injection solution) of wet portion 151 into the dry portion 152 prior to activation of the automatic injection assembly. Generally, seal structure 160 can include an outer sealing member 180, a movable sealing plug 166, a by-pass zone 165, at least one flow path 167, and preferably also includes a filter or membrane 164. With reference to FIGS. 5A–D, seal structure 160 can preferably be formed as a six piece (FIG. 5A), five piece (FIG. 5B), four piece (FIG. 5C), or three piece (FIG. 5D) configuration.

Figure 5A:
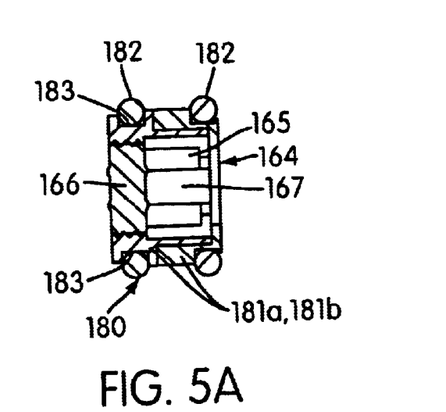
FIGS. 5A–5D illustrate cross-sectional side views of various embodiments of a seal structure according to the present invention.

More particularly, with reference to FIG. 5A, the outer sealing structure 180 of the six piece configuration can comprise a two piece annular rigid body 181 wherein members 181a, 181b thereof are formed into the two piece rigid body using, e.g., annular weld connections or other bonding techniques known in the art. Outer sealing structure 180 can further include multiple external sealing members 182, e.g., two O-rings, to provide an annular sealing engagement with the inner wall of vial or compartment 150. The sealing structure 180 further includes an internal plug member 166 and a filter or dispersion membrane 164 as will be discussed in greater detail later.

Figure 5B:
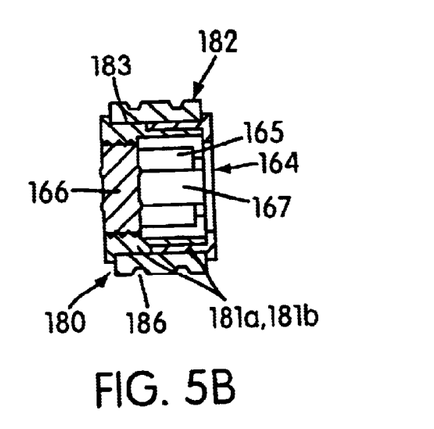

In another embodiment, as shown in FIG. 5B, rather than plural O-rings, outer sealing structure 180 can include a single external sealing member 182, e.g., a unitary gasket, to provide an annular sealing engagement with the inner wall of vial or compartment 150. External sealing member 182 may optionally be secured to two piece rigid body 181 using any bonding techniques known in the art. Further, rigid body members 181a, 181b may be shaped such that they securingly engage external sealing members 182 within notched recesses 183. Alternately, sealing members 182 may be secured to rigid body members 181a, 181b by an interference fit. As with the first embodiment, a filter or membrane 164 is clamped in place at the proximal end of flow path 167 between member 181a and member 181b of the two piece rigid body.

Figure 5C:
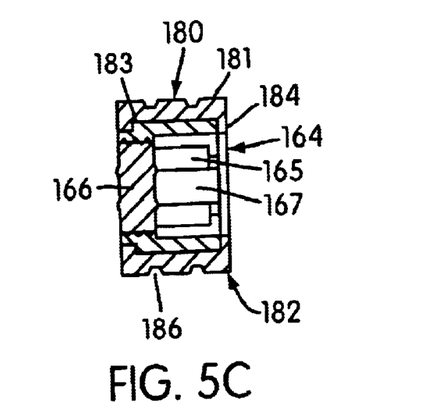
Figure 5D:
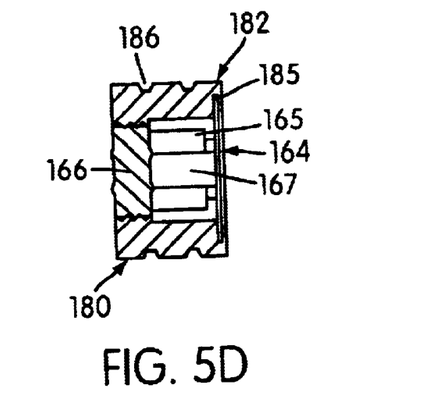
Figure 6A:
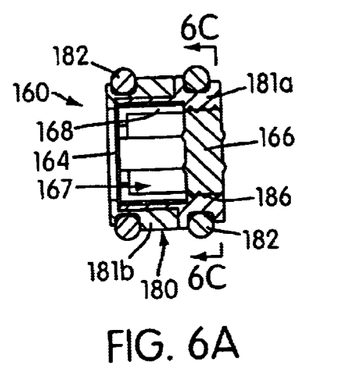
FIG. 6A is a longitudinal cross-sectional side view of a seal structure in accordance with another embodiment of the present invention, wherein the movable sealing plug is in a closed sealing position blocking the flow of the liquid injection solution.
Figure 6B:
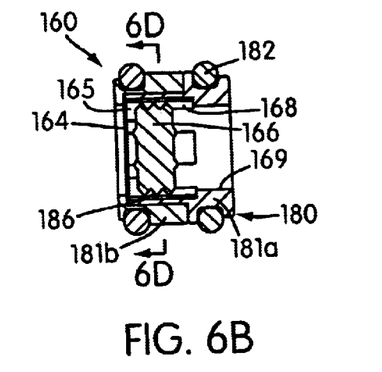
FIG. 6B is a longitudinal cross sectional side view of seal structure similar to 6A, but showing the movable sealing plug in an open by-pass position permitting the flow of the liquid injection solution.
Figure 6C:
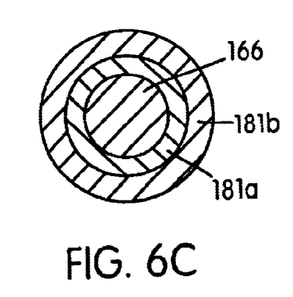
FIG. 6C is a lateral cross sectional view of the seal structure of the present invention taken through the line 6C—6C in FIG. 6A.
Figure 6D:
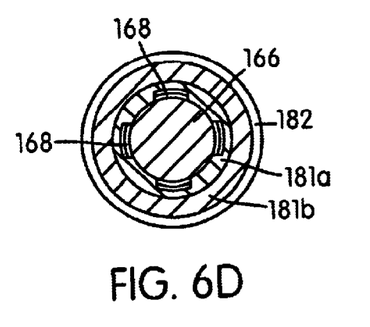
FIG. 6D is a lateral cross sectional view of the seal structure of the present invention taken through the line 6D—6D in FIG. 6B.

In another embodiment, as shown in FIG. 5C, outer sealing structure 180 comprises a unitary internal rigid member 181 and an external sealing member 182. Again, internal rigid member 181 and external sealing member 182 may optionally be secured together using any bonding techniques known in the art. Further, internal rigid member 181 and external sealing member 182 may be formed such that they securingly engage each other using a combination of notched recesses 183 and extending shoulders 184. The filter or membrane 164 can be held in place between internal rigid member 181 and shoulder 184 of external sealing member 182. In yet another embodiment, as shown in FIG. 5D, outer sealing object 180 can comprise a unitary external sealing member 182 which can optionally be molded so as to accommodate filter or member 164 within retaining recess 185. FIGS. 6A and 6B illustrate another embodiment that is very similar to that of FIG. 5A, but provides a slightly different shape for outer annular rigid body 181 and particularly the members 181a, 181b thereof.

In each embodiment illustrated in FIGS. 5A–5D and 6A–6B, external sealing member 182 is preferably formed from a non-reactive elastomer material which can provide for the necessary sealing engagement with the inner wall of vial or compartment 150. Further, external sealing member 182 can optionally be lubricated with silicon or other suitable non-reaction lubricant to facilitate movement of the outer sealing object 180 forwardly within vial or compartment 150 upon receiving sufficient force as will be described. The movable sealing plug 166 is preferably formed from a material having low frictional properties such that the sealing plug 166 may easily slide within outer sealing object 180 when the injector is activated. The movable sealing plug 166 may also optionally be lubricated with silicon or other suitable non-reactive lubricant. In each of the embodiments illustrated, the outer annular structure 180 defines an inner surface having a smooth cylindrical configuration towards the rearward portion 169 thereof, and longitudinally extending grooves 168 towards the forward portion thereof. The grooves 168 create a flowpath or flowpaths 167 through which liquid in the wet compartment 151 can bypass seal plug 166 when the plug 166 is moved forwardly from sealing engagement with cylindrical surface portion 169 into the grooved portion 168. The movement of the sealing plug 166 into the by-pass area 165 opens the fluid flow path 167 between wet portion 151 and dry portion 152. The movable sealing plug 166 preferably includes a plurality of circumferential grooves 186 to provide for enhanced sealing engagement and to facilitate sliding action of the plug 166.

As mentioned above, the seal structure 160 preferably includes filter or membrane 164 at the end of flow path 167 through which the liquid injection solution may pass after the injector has been activated. The liquid injection solution then enters the dry portion 152 of the chamber 150 where it mixes with and dissolves the dry medicament. More particularly, the filter 164 disperses the liquid injection solution exiting the seal structure 160 to present laminar fluid flow to the full surface of the dry medicament, thereby wetting the entire surface of the dry medicament for rapid and complete dissolution. The filter membrane 164 can be any structure that generally uniformly distributes the liquid across the entire diameter of the chamber 150 for enhanced dissolution of the dry medicament.

During operation, manual activation of the actuator assembly 120 releases the collet 122 (as described above), which applies pressure on the plunger assembly 170. The application of pressure on the plunger assembly 170 by the collet and spring assembly 124 moves the plunger 170 in the direction of the needle assembly 140. As a result, the entire chamber 150 and needle assembly 140 are moved forwardly in the housing 110 such that needle 141 pierces through the front end of sheath 202 and exits through the forward end of the housing 110, and particularly through a hole 204 in the front nose-cone portion 206 of the housing. The sheath 202, which serves to maintain the needle 141 sterile when the injector is in storage, also serves as a shock absorber during activation as it is compressed in generally accordion like fashion between the nose cone 206 and needle support 143.

When the needle 141 is extended from the housing 110 and the chamber 150 and needle support 143 approach the nose cone 206 portion of the housing so that further forward movement of chamber 150 is substantially resisted, the plunger 170 then begins to travel forwardly through the chamber 150. This pressurizes the liquid injection solution located within the wet compartment 151. With reference to FIGS. 6A–6B, the increased pressure within the wet compartment 151 moves the sealing plug 166 from a first sealed position wherein sealing plug 166 is sealingly engaged with surface 169 of outer sealing structure 180 (FIG. 6A) to a second by-pass position (FIG. 6B) that allows the injection solution to flow through flow path 167 created by grooves 168 and thereby through seal structure 160.

As described above, the high pressure developed within the wet portion 151 in response to movement of the collet 122 and the plunger assembly 170 forces the liquid injection solution through the seal structure 160 dissolving the drug into a medicament injection solution which will then be forced out through the needle 141 and into the patient. As the collet 122 and plunger assembly 170 continue forward, the plunger 170 will eventually contact the seal structure 160, which, in a preferred embodiment, causes the seal structure 160 to move in the direction of the needle assembly 140. Movement of the seal structure 160 would cause any remaining solution within the portion 152 to be dispersed through the needle assembly 140, so as to reduce the amount of residual medicament remaining within the chamber 150.

Referring to FIGS. 2A, 2B and 4, a membrane or filter 190 is preferably provided adjacent the needle assembly 140 to prevent any dry medicament particles from clogging the rearward end of needle 141 prior to an injection operation. The membrane 190 may also serve to slightly restrict or slow injection of medicament into the patient, to facilitate more thorough dissolution during injection.

More particularly, to prevent the passage of undissolved dry medicament to the needle assembly 140, a medicament support 190 is preferably provided between the end of the dry compartment 152 and the needle assembly 140. The support 190 can serve to prevent blockage of the needle assembly 141 by preventing the dry medicament from entering the area surrounding the needle assembly 140 while permitting passage of the mixture of dissolved medicament and liquid injection solution. The support 190 may be configured as described in U.S. Provisional Application No. 60/238,448, which is herein incorporated by reference in a manner consistent with this disclosure. It is contemplated that multiple supports 190 may be located within the dry compartment 152. The provision of the supports 190 may also improve the laminar flow of the liquid injection solution through the dry medicament thereby improving dissolution.

Further, a diaphragm assembly (not shown) may also be provided adjacent the medicament support 190, as known in the art. The diaphragm assembly acts to prevent the passage of the liquid injection solution to the needle assembly 140 prior to activation of the actuator assembly 120. More particularly, the diaphragm assembly will not rupture until either the butt end of the needle assembly 140 ruptures the expanded diaphragm or sufficient pressure builds in the dry compartment 160 to rupture the diaphragm, again as known in the art.

As discussed above, the movement of the collet 122 causes the injection needle 141 of the injection assembly 140 to advance and protrude through the housing 110. As such, the injection of the medicament can be performed with a simple operation. In sum, the user simply removes the end cap assembly 130, locates the injection end of the housing 110 adjacent the injection site, and presses the push button 132. This operation automatically triggers the operation of the drive assembly or spring 250 to advance the collet 122 causing the liquid injection solution located within the wet portion 151 to enter the dry portion 152 through the seal structure 160. The dissolved medicament is then transmitted through the injection needle 141 to provide the user with the necessary dose of medicament. The automatic injector 10 in accordance with the present invention reduces the amount of time required to administer medicament compared to other wet/dry injectors and eliminates the need for mixing by the user.

The seal structure 160 advantageously enables the manufacture of a superior wet/dry auto injector with a complementary combination of components that are either known in the art of conventional auto-injectors or are otherwise relatively simple to manufacture. The seal structure 160 enables sufficient mixing of wet and dry medicament components without requiring manual shaking. This mixing action is enhanced by the filter or membrane 164. In a preferred embodiment, the filter 164 is a supported, hydrophobic acrylic copolymer cast on a non-woven nylon support. Preferably, it is a FlouRepel treated membrane for superior oleophobicity/hydro-phobicity.

Figure 8A:
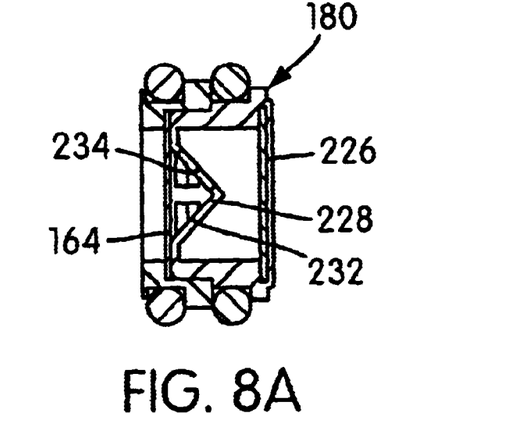
FIGS. 8A and 8B are longitudinal cross sectional views of two additional embodiments of seal structures in accordance with the present invention.
Figure 8B:
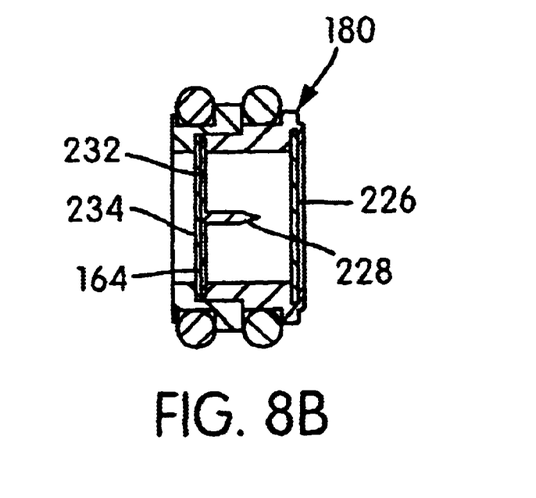

In other embodiments (see FIGS. 8A and 8B), no inner plug 166 is provided. Rather, the outer structure 180 is simply complemented by a seal membrane 226 that extends across the inner area defined by the inner surface of the outer structure. When the chamber 150 reaches the forward end of the housing during an injection operation, pressurization of the wet compartment 151 causes the seal membrane 226 to rupture, thereby allowing the seal structure 160 to permit liquid to pass therethrough. In this embodiment, it may be desirable to provide the seal structure 160 with a pointed member 228 disposed adjacent to the seal membrane 226 to facilitate rupturing of the seal membrane upon pressurized expansion thereof during an injection operation. The member 232 on which the pointed member 228 is mounted has a plurality of passages 234 that permits fluid to pass therethrough. Filter or membrane 164 is preferably mounted distal to the passages 234 to present laminar or distributed flow to the dry medicament.

EXAMPLES

Figure 7:
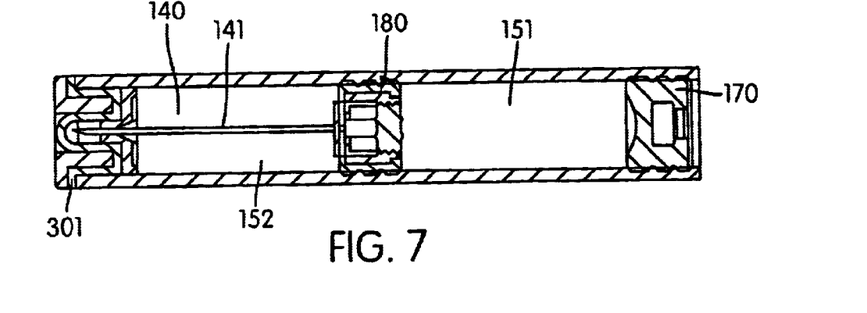
FIG. 7 is a longitudinal cross-sectional view of a wet/dry automatic injector cartridge or chamber configuration in accordance with another embodiment of the present invention.

In another embodiment, clearly shown in FIG. 7, the automatic injector cartridge includes a needle assembly 140 located within the dry portion 152. The needle assembly 140 extends within the dry portion 152 to the sealing structure 180, described above in connection with FIGS. 5A–5D. The sealing structure 180 separates the dry portion 152 from the wet portion 151. As shown in FIG. 7, the cartridge further includes a plunger 170 positioned therein. The plunger 170 is configured to engage the collet 122 of the activation assembly 120. As clearly visible in FIG. 7, the cartridge includes a sheath 301. Like the sheath 202, the sheath 301 maintains the needle 141 in a sterile environment until it projects from the end of the sheath 301 in response to activation of the activation assembly 120. During operation, the needle assembly 140 passes through the dry portion 152 as the wet medicament passes through the sealing structure 180.

An injector according to the present invention was loaded with liquid injection solution and dry medicament and activated with the follow results.

| Loaded | | Dispensed | | Operational |
|---|---|---|---|---|
| Dry Powder | Fluid | Dry Powder | Fluid | Time |
| mg | Ml | % | mg | ml | Secs. |
| 531 | 2.7 | 94 | 497 | 2.3 | 4.0 |
| 557 | 2.7 | 93 | 515 | 2.3 | 4.5 |
| 582 | 2.6 | 92 | 537 | 2.2 | 4.4 |

It will be apparent to those skilled in the art that various modifications and variations may be made without departing from the scope of the present invention. For example, it is contemplated that a cover assembly, described for example in U.S. Pat. No. 5,295,965 (the disclosure of which is specifically incorporated herein by reference) may be secured to the injection end of the housing 110 after deployment of the medicament. Furthermore, the automatic injector may further include a nipple plunger assembly, as described for example in U.S. Pat. No. 5,465,727 (the disclosure of which is specifically incorporated herein by reference).

In yet a further embodiment, the forward dry chamber 152 contains the needle 141, as shown in FIG. 7. The needle 141 is forced through a forward plug stopper upon initial compression of the two chamber system. As known in the art, providing the needle in the forward chamber provides improved longitudinal compactness of the design.

In yet another embodiment, a pre-filled syringe is provided with the seal structure disposed between wet and dry components.

In further contemplated embodiments, the seal structure 160 can be used in the same type of injector described herein, except rather than employing a dry (powder) medicament separated by a liquid component, a first liquid medicament is separated from a second fluid component by the seal structure 160. In yet another embodiment, the seal structure 160 can be used in what is known in the art as a "needleless injector" where an injection can be made into a patient without a needle or cannula. Thus, it is intended that the present invention covers the modifications and variations of the invention, provided they come within the scope of the appended claims and their equivalents.

What is claimed is:

1. An automatic injection device containing a pre-loaded charge of medicament for automatically self-administering the medicament upon actuation thereof, the device comprising:

a housing assembly having an interior chamber, the interior chamber including a dry compartment containing a dry medicament component, and a wet compartment containing a liquid component to be mixed with the dry component;

a seal structure between the dry compartment and the wet compartment, the seal structure being initially in a sealing condition that maintains the dry component sealed from the wet component, the seal structure including at least one flow path formed therein, the seal structure being converted to a mixing condition as a result of activation of the device;

a fluid distributing member disposed between the liquid component and the dry medicament component;

a needle assembly that dispenses the charge of medicament from the housing;

an activation assembly carried by the housing and including a stored energy source, wherein activation of the activation assembly releases the stored energy from the stored energy source, and wherein the release of the stored energy causes a) the seal structure to be converted from the sealing condition to the mixing condition and thereby permit the liquid component to pass through the at least one flow path from the wet compartment to the dry compartment, b) the liquid component to be forced through the fluid distributing member and distributed to the dry component and facilitate mixing and dissolution of the dry medicament component in the liquid component, and c) force the mixed liquid and dry components through the needle assembly.

2. An automatic injection device according to claim 1, wherein said seal structure includes an outer seal member and an inner seal plug movable with respect to said outer seal member from a sealing position which seals the wet compartment from the dry compartment and a mixing position allowing contents of the dry and wet compartments to mix.

3. The automatic injection device according to claim 2, wherein the inner side wall of the outer seal member includes grooves which enable flow of the liquid injection solution around the seal plug and through the seal structure when said seal plug is moved to the mixing position.

4. The automatic injection device according to claim 2, wherein the outer seal member of the seal structure comprises an external sealing member and an internal rigid body configured so as to securingly engage each other.

5. The automatic injection device according to claim 4, wherein the internal rigid body is formed from two rigid members which are annularly welded or bonded together.

6. The automatic injection device according to claim 5, wherein the seal structure further includes a filter or membrane assembly which is clamped between the two rigid members of the internal rigid body, whereby the filter or membrane assembly creates a laminar fluid flow as the liquid injection solution passes from through the seal structure from the wet compartment to the dry compartment.

7. The automatic injection device according to claim 1, wherein the needle assembly comprises a membrane adjacent the dry compartment, wherein the membrane prevents undissolved dry medicament from entering the needle assembly.

8. The automatic injection device according to claim 1, wherein the interior chamber has an open-mouth configuration at the end of the dry compartment adjacent the needle assembly.

9. An automatic injection device according to claim 1, wherein the fluid distributing member includes a filter or membrane assembly which creates a laminar fluid flow as the liquid injection solution passes through the seal structure from the wet compartment to the dry compartment;

wherein the needle assembly comprises a membrane adjacent the dry compartment, wherein the membrane prevents undissolved dry medicament from entering the needle assembly.

10. An automatic injection device according to claim 1, wherein the fluid distributing member comprises a filter.

11. An automatic injection device according to claim 10, wherein the filter creates a laminar fluid flow as the liquid solution passes through the seal structure.

12. An automatic injection device according to claim 1, wherein the seal structure comprises a sealing assembly and a plug member carried by the sealing assembly.

13. An automatic injection device according to claim 12, wherein the sealing assembly has an outer periphery that forms a peripheral seal with an interior wall of the interior chamber, and wherein said plug member is spaced radially inward from the peripheral seal that seals the at least one flow path formed in the seal structure.

14. An automatic injection device according to claim 1, wherein the activation assembly includes a pre-compressed spring.

15. An automatic injection device according to claim 1, wherein the seal structure and the distributing member are integrated into a single assembly.

16. An automatic injection device according to claim 1, wherein the needle assembly is disposed toward a forward end of the housing assembly and the activation assembly is disposed toward a rearward end of the housing assembly, wherein the dry medicament component is disposed forwardly of the liquid component.

17. An automatic injection device according to claim 16, wherein the activation assembly includes a pre-compressed spring that urges a collet rod forwardly through the housing, and wherein forward movement of the collet rod creates sufficient pressure on the liquid component to cause the liquid component to force the seal structure into the mixing condition.

18. An automatic injection device according to claim 17, wherein the seal structure is movable forwardly with respect to the housing as the collet rod is moved forwardly.

19. An automatic injection device according to claim 16, further comprising a dry medicament support structure disposed between the dry medicament component and the needle assembly.

20. An automatic injection device according to claim 1, wherein the seal structure incorporates a burstable membrane.

21. An automatic injection device containing a pre-loaded charge of medicament for automatically self-administering the medicament upon actuation thereof, the device comprising:
- a housing assembly having an interior chamber, the interior chamber including a dry compartment containing a dry medicament component, and a wet compartment containing a liquid component to be mixed with the dry component;
- a seal structure between the dry compartment and the wet compartment, the seal structure being initially in a sealing condition that maintains the dry component sealed from the wet component, the seal structure being converted to a mixing condition as a result of activation of the device;
- the seal structure having a periphery that forms a peripheral seal slidably disposed with respect to an adjacent surface of the interior chamber, the seal structure having an inner seal member spaced radially inward from the peripheral seal that seals at least one flow path formed in the seal structure prior to activation of the device, the inner seal member being convertible from a sealing condition to a mixing condition to enable fluid to flow through the at least one flow path in the seal structure from the wet compartment to the dry compartment;
- a needle assembly that dispenses the charge of medicament from the housing;
- an activation assembly carried by the housing and including a stored energy source, wherein activation of the activation assembly releases the stored energy from the stored energy source, and wherein the release of the stored energy causes a) the seal structure to be converted from the sealing condition to the mixing condition and thereby permit the liquid component to pass through the at least one flow path, b) force the mixed liquid and dry components through the needle assembly.

22. An automatic injection device according to claim 21, wherein the seal structure incorporates a burstable membrane.

23. An automatic injection device according to claim 21, wherein the inner seal member is a movable plug.

24. An automatic injection device according to claim 21, further comprising a fluid distributing member disposed between the liquid component and the dry medicament component.

25. An automatic injection device according to claim 24, wherein the fluid distributing member comprises a filter.

26. An automatic injection device according to claim 24, wherein the fluid distributing member moves from an initial position spaced rearwardly from the needle assembly to a final position disposed closer to the needle assembly relative to the initial position.

27. An automatic injection device according to claim 21, wherein the seal structure moves from an initial position spaced rearwardly from the needle assembly to a final position disposed closer to the needle assembly relative to the initial position.

28. An automatic injection device according to claim 21, wherein the activation assembly includes a pre-compressed spring.

29. An automatic injection device according to claim 21, wherein the seal structure and the distributing member are integrated into a single assembly.

30. The automatic injection device according to claim 21, wherein the needle assembly comprises a membrane adjacent the dry compartment, wherein the membrane prevents undissolved dry medicament from entering the needle assembly.

31. The automatic injection device according to claim 21, wherein the interior chamber has an open-mouth configuration at the end of the dry compartment adjacent the needle assembly.

32. An automatic injection device according to claim 21, wherein the seal structure further includes a filter or membrane assembly which creates a laminar fluid flow as the liquid injection solution passes through the seal structure from the wet compartment to the dry compartment;
- wherein the needle assembly comprises a membrane adjacent the dry compartment, wherein the membrane prevents undissolved dry medicament from entering the needle assembly.

33. A method of administering a pre-loaded charge of medicament, comprising:
- providing an automatic injection device having a housing assembly, wherein the housing assembly includes an interior chamber having a dry compartment containing a dry medicament component, and a wet compartment containing a liquid component to be mixed with the dry component, the injection device further includes a seal structure between the dry compartment and the wet compartment, the seal structure being initially in a sealing condition that maintains the dry component sealed from the wet component, the seal structure being converted to a mixing condition as a result of activation of the device, a fluid distributing member disposed between the liquid component and the dry medicament component, a needle assembly that dispenses the charge of medicament from the housing, and an actuating assembly having stored energy source;
- locating the automatic injection device at a desired location on a recipient; and
- actuating the activation assembly carried by the housing to release the stored energy from the stored energy source such that the release of the stored energy causes a) the seal structure to be converted from the sealing condition to the mixing condition and thereby permit the liquid component to pass there through, b) the liquid component to be forced through the fluid distributing member and distributed to the dry component and facilitate mixing and dissolution of the dry medicament component in the liquid component, and c) force the mixed liquid and dry components through the needle assembly.

\* \* \* \* \*